(12) United States Patent
Rosenblum et al.

(10) Patent No.: US 6,750,329 B1
(45) Date of Patent: Jun. 15, 2004

(54) ANTIBODY DELIVERY SYSTEM FOR BIOLOGICAL RESPONSE MODIFIERS

(75) Inventors: Michael G. Rosenblum, Sugar Land, TX (US); Clyde W. Wellen, Houston, TX (US)

(73) Assignee: Research Development Foundation, Carson City, NV (US)

( * ) Notice: Subject to any disclaimer, the term of this patent is extended or adjusted under 35 U.S.C. 154(b) by 0 days.

(21) Appl. No.: 08/251,574

(22) Filed: May 31, 1994

Related U.S. Application Data

(63) Continuation-in-part of application No. 08/119,505, filed on Sep. 10, 1993, which is a continuation-in-part of application No. 07/951,357, filed on Sep. 25, 1992, now abandoned, which is a continuation of application No. 07/348,237, filed on May 5, 1989, now abandoned.

(51) Int. Cl.[7] ............................................. C07K 17/00
(52) U.S. Cl. ................ 530/391.7; 530/387.3; 530/351; 530/387.1; 530/388.8
(58) Field of Search ............... 530/391.7, 387.3, 530/351, 387.1, 388.8

(56) References Cited

U.S. PATENT DOCUMENTS 4,671,958 A * 6/1987 Rodwell .................. 424/130.1

FOREIGN PATENT DOCUMENTS

| EP | 256714 | * | 2/1988 |
| EP | 281070 | * | 9/1988 |
| WO | 8809344 | * | 12/1988 |
| WO | 8906692 | * | 7/1989 |

OTHER PUBLICATIONS

Schulz et al. PNAS vol. 80 p. 5407–5411, Sep. 1983.*
White et al Cancer Research 45(3) 1985 1337–1343.*

* cited by examiner

Primary Examiner—Sheela J. Huff
(74) Attorney, Agent, or Firm—Fulbright & Jaworski L.L.P.

(57) ABSTRACT

The present invention provides a novel conjugate comprising an antibody directed toward a cell surface associated antigen, wherein said antigen is selected from the group consisting of 15A8 antigen and ZME-018 antigen; and a biological response modifier moiety, wherein said moiety is selected from the group consisting of TNF-alpha, TNF-beta and Interleukin-1. In addition, the present invention also provides a method of treating proliferative cell diseases comprising administration of a cytocidally effective dose of the composition of Claim 1 individual in need of said treatment.

4 Claims, 10 Drawing Sheets

ANTIBODY DELIVERY SYSTEM FOR BIOLOGICAL RESPONSE MODIFIERS

CROSS REFERENCE TO RELATED APPLICATIONS

This application is a continuation in part of U.S. Ser. No. 08/119,505, filed Sep. 10, 1993, which is a continuation of U.S. Ser. No. 07/951,357, filed Sep. 25, 1992, now abandoned, which is a continuation of U.S. Ser. No. 07/348,237, filed May 5, 1989, now abandoned.

BACKGROUND OF THE INVENTION

1. Field of the Invention

The present invention relates generally to the field of immunoconjugates. More specifically, the invention relates to conjugates of monoclonal antibodies and biological response modifiers.

2. Description of the Related Art

Biological response modifiers exhibit a variety of effects upon a number of cell types. Mammalian cells produce lymphokines and cytokines to maintain homeostasis at the cellular level. At physiological or in pharmacological concentrations, biological response modifiers such as the interferons, the interleukins and tumor necrosis factor (TNF) all have cytotoxic effects. TNF has pleotropic and anti-tumor effects on animal and human tumor cells in vitro and in vivo. Recombinant human TNF has been shown to cause tumor necrosis of sarcoma, adenocarcinomas, and melanomas. TNF has divergent effects on cell growth, causing anti-growth effects on some cell lines, virtually no effect on other lines, and growth enhancement of other cells. TNF may also increase bone-resorption and enhance pro-coagulant activity of endothelial cells.

When drugs or other cytoactive agents are administered to an individual, many, if not all, are diluted in the host body and are, to a certain extent, metabolized by the host tissues. Thus, in many cases these cytoactive agents must be administered in much higher amounts than are necessary to achieve the desired effects in order to account for the dilution, absorption, and metabolism by non-target tissues.

Cancer is one of the leading causes of mortality and morbidity in the Western world. Breast cancer and cervical cancer are two of the leading causes of death from malignancy in women in the Western world. Melanoma is a highly metastatic disease affecting both sexes and is almost uniformly fatal within five years of diagnosis. Surgical removal of localized malignancies has proven effective only when the disease has not spread beyond the primary lesion. Once the disease has spread, the surgical procedures must be supplemented with other more general procedures to eradicate the diseased or malignant cells. Most of the commonly utilized alternative therapeutic modalities such as irradiation or chemotherapy do not confine their effects solely to the tumor cells and, although they have a proportionally greater destructive effect on malignant cells, often affect normal cells to some extent.

Many tumors or cancer cells express membrane-bound or cytoplasmic antigens or antigenic determinants which are either expressed very weakly or not at all by normal cells. Some tumor cells express antigens also found in or on embryonic cell types but are not expressed by normal cells of a mature animal. These abnormally expressed antigens are known as tumor-associated antigens. These tumor-associated antigens may be expressed on the surface of the cell (cell surface antigen), may be secreted by the tumor cell (secreted antigens) or may remain inside the cell (intracellular antigen). While membrane-bound or cell-surface antigens are believed to play a major role in the interaction between tumor cells and the host's immune system, cytoplasmic antigens are also useful for monitoring neoplasia since these antigens are often shed in large amounts by the tumor cells.

Antibodies are proteins normally produced by the immune system of an animal in response to foreign antigens or antigenic determinants. Antibodies bind to the specific antigen to which they are directed. Monoclonal antibodies directed to specific antigens or antigenic determinants may be prepared in large quantities. Monoclonal antibodies to tumor associated antigens localize in tumors after systemic administration to patients with cancer.

Antibodies, coupled to drugs, have been used as a delivery system by which the drug is targeted to a specific tumor cell type against which the antibody is directed. The linking of cytotoxic agents to antibodies to make "immunotoxins" has been reported. Of particular interest have been immunotoxins of monoclonal antibodies conjugated to the enzymatically active portions (A chains) of toxins of bacterial or plant origin such as Ricin or Abrin. Nevelle and York, Immunol. Rev. (1982) 62: 75–91; Ross et al., European J. Biochem. (1980) 104; Vitteta et al., Immunol. Rev. (1982) 62: 158–183; Ross et al., Cancer Res. (1982) 42: 457–464; Trowbridge and Domingo Nature (Cond.) (1981) 294: 171–173. Immunotoxins have been prepared by conjugating MoAbs with toxins or fragments of toxins derived from plants. Gelonin and ricin are among the most active plant derived toxins in inhibiting protein synthesis.

Although antibodies have been used as delivery systems for toxic moieties of plant toxins and other cytotoxic drugs, conjugation of antibodies to biological response modifiers such as tumor necrosis factor and the use of such conjugates as specific delivery system to target tissues or cells has not heretofore been possible.

The prior art remains deficient in the lack of effective means to treat a wide variety of human cancers. The prior art fulfils this longstanding need and desire in the art.

SUMMARY OF THE INVENTION

The present invention is directed to a novel antibody delivery system for biological response modifiers. The present invention provides a composition which is an immunoconjugate of an antibody directed toward a cell associated antigen covalently bound to a biological response modifier. Preferably, the antibody is directed toward a cell associated antigen specific for a tumor cell. In one embodiment, the immunoconjugate comprises an antibody, preferably a monoclonal antibody covalently coupled to a biological response modifier. Alternatively, the immunoconjugate may be a fusion protein prepared by genetic engineering methods known to those in the art. Such a fusion protein would contain the antigen recognition site of an antibody molecule and the cytotoxic moiety of a biological response modifier.

In one embodiment, the invention provides a cytotoxic composition which selectively binds to and kills tumor cells. These target tumor cells may be of any tumor which has or produces an antigenic marker in amounts greater than that found in or on normal cells. While preferably the antigenic marker is a cell surface antigen, the present invention is equally applicable to tumor cells which produce an intracellular antigen in amounts greater than normally produced by normal cells. It is known that many tumors produce intracellular antigens and either secrete them or release these antigens when the tumor becomes necrotic.

It can readily understood that the immunoconjugate of the present invention may be utilized to target delivery, not only of cytotoxic Biological Response Modifiers to selected target cells, but also to selectively deliver any biological effector to a selected target site as long as said target site contains an antigenic marker at a concentration in excess of that found at other non-target sites.

In another embodiment, the invention provides cytotoxic compositions which selectively bind to and are cytotoxic for or cytostatic for human breast cancer cells, cervical carcinoma cells, and melanoma cells. In another embodiment, this invention provides a method of killing human breast cancer cells, cervical carcinoma cells, melanoma cells or other tumor cells expressing tumor associated antigen by contacting the cells with a cytocidally effective amount of the immunotoxin composition of the present invention. In one embodiment, the immunoconjugate of the present invention is used to deliver a cytotoxic immunoconjugate to breast tumor cells which express the 15A8 antigen. In yet another embodiment the present invention provides an immunoconjugate that binds to and is cytotoxic or cytostatic for melanoma tumor cells. In yet another embodiment the present invention provides an immunoconjugate that binds to and is cytotoxic or cytostatic for cells which express the ZME-018 antigen or a functional equivalent thereof. The immunoconjugate of the present may also comprise an antibody which recognizes a cytoplasmic antigen including, but not limited to, the 465.12 antibody of Wilson which reacts with a melanoma cytoplasmic antigen.

It is an object of the invention to provide conjugates of antibodies with biological response modifiers.

It is another object of the present invention to provide a composition of matter comprising a conjugate of an antibody directed toward a tumor associated antigen and a biological response modifier moiety.

It is another object of the present invention to provide a composition comprising a recombinantly produced compound comprising an antibody moiety and a biological response modifier, which biological response modifier may be an cytoactive moiety of said biological response modifier.

Another object is to provide a method of treating proliferative cell diseases such as, for instance, cancer, comprising administration of a cytocidally effect dose of an immunoconjugate comprising an antibody or antibody moiety directed to a TAA on the target cell conjugated with a biological response modifier or cytoactive moiety thereof to an individual in need of said treatment.

It is a further object to provide an immunoconjugate that is a gene-fusion product recombinantly produced by fusion of a gene coding for the antigen recognition site of a monoclonal antibody with a gene coding for a biological response modifier or the cytoactive moiety thereof, such as cytokines or lymphokines, and preferably TNF.

It is a further object to provide a method of suppressing secondary cataract formation which comprises administration of the immunoconjugate of the present invention to an individual after the surgical replacement of the optic lens.

It is a further object of the present invention to provide a composition comprising an antibody directed to a tumor-associated antigen such as a breast tumor associated antigen or a melanoma conjugated with a biological response modifier such as TNF.

It was a further object of the present invention to provide a pharmaceutical composition comprising an immunoconjugate of a biological response modifier such as TNF in a pharmaceutically acceptable carrier.

An exemplary sample of hybridoma ZME-018 which produces an antibody recognizing the ZME-018 antigen was deposited on Apr. 7, 1992 with the American Type Culture Collection at 12301 Parklawn Drive, Rockville, Md., and received the accession designation HB 11009.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

Figure 1:
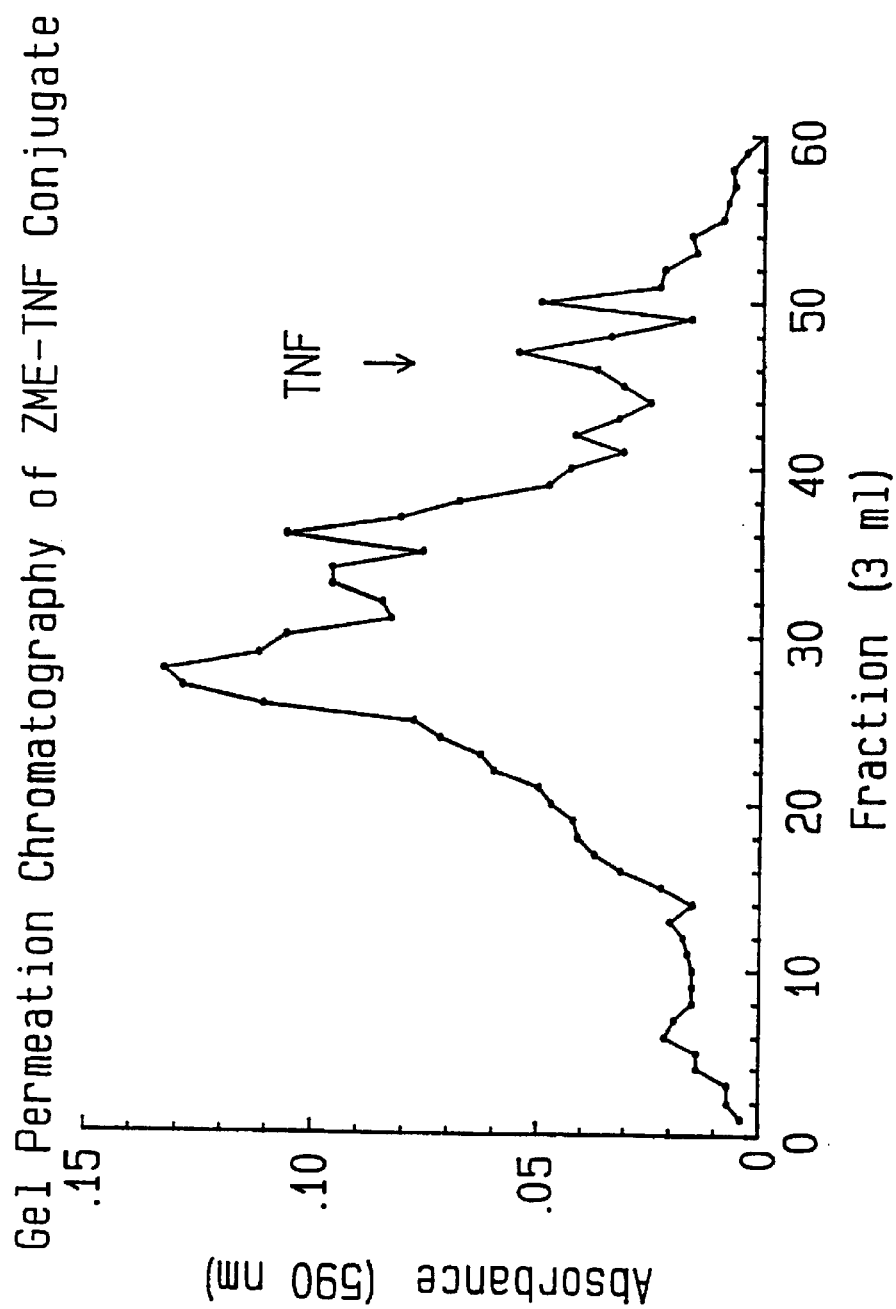
FIG. 1 shows a S-300 Gel Permeation Chromatograph of the ZME-TNF reaction mixture.

The present invention provides a conjugate, comprising an antibody directed toward a cell surface associated antigen, wherein said antigen is selected from the group consisting of 15A8 antigen and ZME-018 antigen; and a biological response modifier moiety, wherein said moiety is selected from the group consisting of TNF-alpha, TNF-beta and Interleukin-1. It is specifically contemplated that the conjugate may be recombinantly produced. A person having ordinary skill in this art would readily recognize the advantages of producing a recombinant conjugate. More specifically, one with ordinary skill in this art would, without undue experimentation, be able to make a conjugate that is a gene-fusion product recombinantly produced by fusion of a gene coding for the antigen recognition site of a monoclonal antibody with a gene coding for a biological response modifier.

In the present invention, it is generally considered that the moiety will be cytotoxic, although it could be non-toxic if desired. Preferably, the conjugate has as its cytotoxic moiety tumor necrosis factor.

The present invention also provides a method of treating proliferative cell diseases comprising administration of a cytocidally effective dose of the composition of Claim 1 individual in need of said treatment. Preferably, the proliferative cell disease is cancer. Most preferably, the cancer is selected from the group consisting of breast cancer, cervical carcinoma and melanoma.

In addition, the present invention also provides other methods, including a method of treating human breast carcinoma comprising administration of a cytotoxic or cytostatic dose of TNF-conjugated monoclonal antibody 15A8 to an individual diagnosed as having a tumor bearing 15A8 tumor associated antigen. The present invention also provides a method of treating cervical carcinoma comprising administration of a pharmacologically effective dose of TNF-conjugated monoclonal antibody directed against 15A8 tumor associated antigen to an individual in need of said treatment. Furthermore, the present invention provides a method of treating melanoma comprising administration of a pharmacologically effective dose of a TNF-conjugated monoclonal antibody ZME-018 to an individual in need of said treatment. Another embodiment of the present invention is a method of suppressing secondary cataract formation which comprises administration of the conjugate of Claim 1 to an individual after the surgical replacement of the optic lens.

The immunochemical derivatives of this invention comprise conjugates of an antibody directed toward a tumor associated antigen and a biological response modifier. Biological response modifiers which may be coupled to the antibody directed toward a tumor associated antigen and used in the present invention include, but are not limited to, lymphokines and cytokines such as TNF (alpha or beta), interleukin, especially IL-1, interferons and IL-6. These biological response modifiers have a variety of effects on tumor cells. Among these effects are increased tumor cell killing by direct action as well as increased tumor cell killing by increased host defense mediated processes. Conjugation of antibody directed to a tumor associated antigen with these biological response modifiers will allow selective localization within tumors and, hence, improved anti-proliferative effects while suppressing non-specific effects leading to toxicity of non-target cells.

Specific antibody delivery of cytotoxins to tumors will provide protection of sensitive sites such as the liver, kidney and bone marrow from the deleterious action of the naturally occurring toxic agents. Use of antibodies conjugated to the biological response modifiers as a delivery system allows lower dosage of the drug itself, since all toxic moieties are conjugated to antibodies which concentrate within the tumor or other target site.

Conjugates of the monoclonal antibody may be made using a variety of bifunctional protein coupling agents. Examples of such reagents are SPDP, IT, bifunctional derivatives of imidoesters such as dimethyl adipimidate.HCl, active esters such as disuccinimidyl suberate, aldehydes such as glutaraldehyde, bis-azido compounds such as bis(p-azidobenzoyl) hexanediamine, bis-diazonium derivatives such as bis-(p-diazonium-benzoyl)-ethylenediamine, diisocyanates such as toluene 2,6-diisocyanate, and bis-active fluorine compounds such as a 1,5-difluoro-2,4-dinitrobenzene.

The antibodies employed in the immunoconjugate are preferably monoclonal antibodies, and most preferably monoclonal antibodies directed against a specific pathological conditions, including, but not limited to, cancers such as breast, cervix, melanoma, etc. The antibodies used in the present invention may also be directed against non-cellular antigens which do not originate in the host such as viruses or viral coat antigens. The immunoconjugate of the present invention when comprised of such non-host antigens provides a selective delivery vehicle for delivering cytotoxic or cytostatic biological response modifiers to pathogenically infected host cells. As used herein the term "monoclonal antibody" means an antibody composition having a homogeneous antibody population. It is not intended to be limited as regards the source of the antibody or the manner in which it is made.

By way of example, breast carcinoma cells express a 22/kD antigen on their cell surface. Antibodies to this antigen have been produced. Hybridomas which secrete specific monoclonal antibodies of the IgG1, IgG2a and IgG2b isotypes which recognize an epitope of this 22/kD antigen have been produced. All isotypes recognize the same epitope of the antigen. For the purpose of further example in describing this invention this epitope will be designated the 15A8 epitope. Thus, all of these antibodies are functionally equivalent. Additionally, in practicing this invention, antibodies which bind to different antigenic determinants on the same antigen, i.e., recognize different epitopes are also functionally equivalent.

Monoclonal antibodies may be made by methods known to those of skill in the art. The procedure for making the hybridoma cell cultures which produce, for instance, 15A8 MAb, is generally known to those with skill in this art. Briefly, mammary tumor cells were injected into BALB/c mice intraperitoneally for three weeks for a total of three to four injections. The spleens were harvested three days after the last injection and a spleen cell suspension was prepared and fused with 107 PAI melanoma cells. The hybrid cells were selected on hypoxanthine aminopterin thymidine (HAT) medium. Further details of the preparation of the hybridomas and characterization of these monoclonal antibodies are provided in the examples below. However, monoclonal antibodies prepared against any tumor associated antigen by any method known in the art may be used in the immunoconjugates of the present invention.

The term "Tumor associated antigen" is meant to comprise any antigen which is found in significantly higher concentrations in or on tumor cells than on normal cells. Although the term "tumor associated antigen" normally does not comprise viral or other non-host cell antigens, as used herein it will be apparent to those in the art that the immunoconjugate of the present inventions may also target biological response modifiers to any cells which has an antigenic concentration significantly different from normal cells. Thus, this invention may also be applied to deliver biological response modifiers to virally infected cells, to cells in which the biological response modifiers has a beneficial rather than a toxic effect and the like; it is not necessary that the target cell be a tumor cell. It is only necessary that the target cell have a specific antigenic determinant the differs either qualitatively or quantitatively from other non-target cells.

Biological response modifiers such as TNF may be obtained from sera of intact animals, culture supernatants of lymph cells or cell lines after the animals or cells had been treated with a substance known to stimulate the proliferation of immune cells (an inducer) or by recombinant technology. The biological response modifier may be obtained from any mammalian source such as, e.g., mouse, rabbit, rat, primate, pig, and human. Preferably such proteins are obtained from a human source, and more preferably are recombinant, human proteins. Thereafter, the serum, supernatant or cell paste is harvested and assayed for biological activity toward a target tumor cell line. The term "recombinant protein" refers to a protein having comparable biological activity to the native protein prepared by recombinant DNA techniques. For use in the present invention the recombinantly produced biological response modifier does not have to be identical in structure nor must it express the identical range of biological activities of the native protein, as long as it retains the activity sought to be delivered to the targeted site.

The biological activity of the biological response modifier and of the immunoconjugated biological response modifier may be measured by methods described in the art. For instance, TNF cytotoxic activity may be measured by using an L-929 fibroblast cell assay system as described in Example 2 below. Antibody such as, e.g., 15A8 or ZME-018 were modified with SPDP as described below and then conjugated with iminothiolane modified TNF as described below. The TNF-conjugated antibody was purified by column chromatography on a Sephadex S-300 column as described below.

The immunochemicals of the present invention may be used to kill tumor cells in vitro as well as in vivo. For instance, in clinical situations where bone marrow metastasis has occurred, the bone marrow may be cleared of tumor cells extracorporeally. This is often necessary when a tumor is radiosensitive and total body radiation is a required treatment. For a patient's own bone marrow to be cleared of tumor cells, it can be removed from the patient prior to radiation, cleared of tumor cells extracorporeally and returned to the patient to replace the bone marrow cells destroyed by radiation. When used to kill human breast cancer cells in vitro for example, the conjugates will typically be added to the cell culture medium at a concentration of at least about 10 nM. The formulation and mode of administration for in vitro use are not critical. Aqueous formulations that are compatible with the culture or perfusion medium will normally be used. Cytotoxicity may be read by conventional techniques to determine the presence or degree of breast cancer cells remaining.

Administration of the immunoconjugates of the present invention to an individual who has been diagnosed as having a tumor with a specific antigenic determinant will allow targeting and concentration of the cytotoxic agent at the site where it is needed to kill the tumor cells. By so targeting the cytotoxic agents, non-specific toxicity to other organs, tissues and cells will be eliminated or decreased.

When used in vivo for therapy, the immunotoxins are administered to the patient in therapeutically effective amounts (i.e., amounts that eliminate or reduce the patient's tumor burden). The immunotoxins will normally be administered parenterally, either intravenously or intraperitoneally. The dose and dosage regimen will depend upon the nature of the cancer (primary or metastatic) and its population, the characteristics of the particular immunoconjugate, e.g., its therapeutic index, the patient, and the patient's history. The amount of immunotoxin administered will typically be in the range of about 0.1 to about 10 mg/kg of patient weight. For parenteral administration, the immunoconjugates will be formulated in a unit dosage injectable form (solution, suspension, emulsion) in association with a pharmaceutically acceptable parenteral vehicle. Such vehicles are inherently nontoxic and nontherapeutic. Examples of such vehicles are water, saline, Ringer's solution, dextrose solution, and 5% human serum albumin. Nonaqueous vehicles such as fixed oils and ethyl oleate may also be used. Liposomes may also be used as carriers. The vehicle may contain minor amounts of additives such as substances that enhance isotonicity and chemical stability, e.g., buffers and preservatives. The immunoconjugate will typically be formulated in such vehicles at concentrations of about 0.1 mg/ml to 10 mg/ml. The immunoconjugate of the present invention is then formulated in a non-toxic, inert, pharmaceutically acceptable carrier medium, preferably at a pH of about 3 to 8, more preferably 6–8.

The dosage level of immunoconjugate will depend on the in vivo efficacy data obtained after preclinical testing and will depend mainly upon the particular biological response modifier used and whether it is used alone or in combination with other drugs or biological response modifiers. The pharmaceutical preparation as described above is suitable for parenteral administration to humans or other mammals in therapeutically effective amounts (i.e., amounts which eliminate or reduce the patient's pathological condition) to provide therapy thereto, the type of therapy being dependent on the specific biological response modifier conjugated to the antibody delivery system.

Antibody-conjugated Biological Response Modifiers such as TNF may be administered in combination with interferon, preferably human β interferon (IFN-β). IFN-β refers to immune interferon having comparable biological activity to native interferon. Preferably the interferon is prepared by recombinant technology.

The following examples provide a detailed description of the preparation, characterization, and use of the immunoconjugate of this invention. These examples are not intended to limit the invention in any manner.

EXAMPLE 1

Purification of TNF

TNF may be purified by techniques known to these in the art. For instance, Aggarwal et al. describes the purification of TNF from various sources including several cell lines of monocytic origin. Aggarwal (1986) Methods of Enzymology 116:448, incorporated herein by reference. This method may also be utilized to purify TNF from other sources.

TNF is preferably obtained by recombinant technology known to those of skill in the art. Such a preparation is, for example, described in detail in U.S. Pat. No. 4,677,063 and European Publication EP 186,214. The TNF preparation used to obtain the following data depicted in the following Examples was obtained from Genentech Corp., South San Francisco, Calif. The human recombinant DNA derived material was purified to homogeneity from extracts of *E. coli*. TNF migrated as a single band with an approximate molecular weight of 18,000 daltons.

EXAMPLE 2
Assay of TNF Cytotoxic Activity

The TNF cytotoxic activity was monitored utilizing the following assay on L-929 cells. Forty thousand murine L-929 fibroblasts in MEM media containing 10% FCS were added to each well of a 96 well plate and incubated 24 hours at 37° C. (5% $CO_2$). Cells were then treated with various amounts of either TNF or TNF-antibody conjugate in medium containing 0.5 g/ml Actinomycin-D for 24 hrs at 37° C. (5% $CO_2$). The cells were washed with phosphate buffered saline (PBS), pH 7.2 and viable cells were stained with crystal violet. The plates were read at 590 nm to determine viable cell number. TNF with a specific activity no lower that $1 \times 10^7$ U/mg was used for conjugation with the antibodies. A unit of TNF activity is the amount of TNF protein which causes 50% inhibition of L-929 cell growth.

EXAMPLE 3
Modification of TNF With Iminothiolane

TNF in phosphate buffered saline was concentrated to approximately 2 milligrams/ml in a Centricon 10 microconcentrator. Triethanolamine hydrochloride (TEA/HCl), pH 8.0 and EDTA were added to a final concentration of 60 mM TEA/HCl and 1 mM EDTA pH 8.0. 2-Iminothiolane stock solution (20 mM) was added to a final concentration of 1 mM and the sample was incubated for 90 minutes at 4° C. under a stream of nitrogen gas.

Excess iminothiolane (IT) was removed by gel filtration on a column of Sephadex G-25 (1×24 cm) pre-equilibrated with 5 mM bis-tris/acetate buffer, pH 5.8 containing 50 mM NaCl and 1 mM EDTA. Fractions were analyzed for protein content in microtiter plates using the Bradford dye binding assay. Briefly, forty microliters of sample, 100 ul of phosphate buffered saline (PBS) and 40 ul of dye concentrate were added to each well. Absorbance at 600 nm was read on a Dynatech Microelisa Autoreader. TNF elutes at the void volume (about fractions 14–20). These fractions are pooled and concentrated by use of a Centricon-10 microconcentrator.

EXAMPLE 4
Monoclonal Antibody to 15A8 Antigen and to Melanoma Antigen ZME-018

These monoclonal antibodies may be made by methods known to those of skill in the art. The procedure for making the hybridoma cell cultures which produce the 15A8 antibodies is described in detail in European Application Publication W0-184-369 (published Jun. 11, 1986). Briefly, mammary tumor cells (Soule, et al, JNCI, 51: 1409–1413 (1973) ATCC Accession No. TB-22) were injected into BALB/c mice intraperitoneally every three weeks for a total of three to four injections. The spleens were harvested three days after the last injection and a spleen cell suspension was prepared and washed by two centrifugations (800×g) in Dulbecco's modified Eagles medium. One hundred and eight immunized mouse spleen cells and 107 PAI myeloma cells were resuspended for fusion in a 45% solution (v/v) of polyethylene glycol 1500. The hybrid cells were selected on hypoxanthine-aminopterin-thymidine (HAT) medium.

Clones of the hybridoma were grown in vitro according to known tissue culture techniques such as is described by Cotten, et al., *Eur. J. Immunol.* 3:136 (1973). Hybridomas producing antibodies which reacted with MCF-7 and/or MDA-157 cells but not human foreskin fibroblast cells were further characterized. The antibodies produced by the 15A8 cell line and hybridomas-producing functionally equivalent antibodies reacted with the 15A8 antigen on MCF-7 cells. They also reacted with 28/31 randomly obtained human mammary carcinomas tested and exhibited a weaker reaction with normal human epithelial cells of breast, renal proximal tubule, bladder skin, esophagus and salivary gland, but cells of substantially no other normal tissue, and was unreactive with 14 of 18 other malignant tissues tested. The 15A8 antibody also reacted with all fibrocystic diseases, normal mammary epithelium, a number of adenocarcinomas and did not react with mesotheliomas. The 15A8 antibody also crossreacts with cervical, colon and prostrate carcinomas.

Representative hybridoma cultures whose cells secrete antibody of the same idiotype, i.e., all recognize the 15A8 epitope, have been deposited at the American Type Culture Collection and have been assigned the accession numbers HB-8655 (for 15A8), HB-9344 (for 15A8 G2a) and HB-9345 (for 15A8 G2b).

As used herein with respect to the exemplified murine monoclonal anti-human breast cancer antibodies, the term "functional equivalent" means a monoclonal antibody that: (1) crossblocks an exemplified monoclonal antibody; (b) binds selectively to cells expressing the 15A8 antigen such as human breast cancer cells; (c) has a G or M isotype; (d) binds to the 15A8 antigen as determined by immunoprecipitation or sandwich immunoassay; and (e) when conjugated to TNF exhibits a tissue culture inhibitory dose (TCID) of at least 50% against at least one of the MCF-7, ME-180, BT-20, or A431 cell lines when used at a dose between 50 and 100 units per ml.

Monoclonal antibodies which bind to melanoma cells were similarly prepared. The details of the preparation of monoclonal antibodies directed to cell surface and cytoplasmic melanoma antigens was described in detail in Wilson et al., *Int. J. Cancer* (1981) 28:293, incorporated herein by reference.

EXAMPLE 5
Modification of Monoclonal Antibody 15A8 or ZME-018 With SPDP

N-succinimidyl 3-(2-pyridyldithio) (propionate) (SPDP) in dimethylformamide was prepared as a stock solution of 3 mg/ml in dry dimethylformamide. Since the crystalline SPDP can undergo hydrolysis, the actual concentration of chemically reactive crosslinker was determined by spectrophotometric methods by analyzing the absorbance at 260-nm in a dual-beam spectrophotometer. The concentration of SPDP stock is calculated from the following equation:

Change in absorbance (260 nm)×(3.01)=mmoles/ml/SPDP 0.02× 103 ml/mmol 0.01

One milligram of monoclonal antibody, for instance, MAb 15A8 or MAb ZME-018 in 0.5 ml of PBS was added to a glass tube. SPDP stock solution was slowly added at a 5-fold molar excess to the tube, mixing constantly. The mixture was incubated for 30 minutes at room temperature, mixing every 5 minutes during the incubation period. Excess unreacted SPDP was removed by gel filtration chromatography on a Sephadex G-25 column (1×24 cm) pre-equilibrated with PBS. Fractions (0.5 ml) were collected during the PBS elution and were analyzed for protein content by the Bradford dye method. Antibody eluted in the void volume (approximately fractions 14–20). These fractions were pooled and the protein concentrated in a Centricon-30 microconcentrator. The Centricon retentate was washed with 100 mM sodium phosphate buffer, pH 7.0 containing EDTA (0.5 mM). The antibody was concentrated to a final volume of approximately 0.5–0.75 ml.

EXAMPLE 6
Conjugation of SPDP-modified Monoclonal Antibody With Iminothiolane-modified TNF Antibody 15A8 and antibody ZME-018 were conjugated to TNF using N-succinimidyl-3-(2-pyridyldithio) propionate (SPDP) and/or iminothiolane (IT) as a coupling agent. The conjugates were tested against Me-180, and AAB-527 cells in a 72-hour tissue culture assay. The antibody conjugates exhibited acceptable antiproliferative activity (TCID 50% of less than 10 units/ml) against both of these cell lines.

Monoclonal antibody 15A8 or ZME-018 modified as described in Example 4 was mixed with an equal weight of TNF modified as in Example 3. This proportion corresponded to a 5-fold molar excess of TNF as compared to antibody. The pH of the mixture was adjusted to 7.0 by the addition of 0.05 M/TEA/HCl buffer pH 8.0 and the mixture was incubated for 20 hours at 4° C. under nitrogen. Iodoacetamide (0.1 M) was added to a final concentration of 2 mM to block any remaining free sulfhydryl groups and incubation was continued for an additional hour at about 25° C. The reaction mixture was stored at 4° C. until purification by gel filtration.

EXAMPLE 7
Purification of TNF-monoclonal Antibody Complexes

Non-conjugated TNF was removed from the reaction mixtures of Example 6 by gel filtration on a Sephadex S-300 column (2.5×50 cm) pre-equilibrated with PBS. Reaction mixtures from Example 6 containing TNF conjugated to MAb ZME were concentrated to approximately 1 ml with a Centricon 30 microconcentrator before loading on the Sephadex column. The column was washed with PBS. One ml fractions were collected and 50 ul aliquots are analyzed for protein by the Bradford dye binding assay.

Free and TNF-conjugated antibody eluted at about fractions 17–40 while, unconjugated TNF elutes at about fractions 46–50. FIG. 1 demonstrates the elution profile of the S-300 column. Elution of free TNF standard (in fraction 46–48) is shown by arrow. Elution of unconjugated ZME antibody occurs at approximately fraction 28. After chromatography of the reaction mixture, fraction 20–40 were pooled. PAGE analysis demonstrated that these fractions contained no free TNF. This elution pattern was confirmed by electrophoresis of 50 ul aliquots on 5–20% gradient non-reducing SDS polyacrylamide gels. This analysis confirmed that the conjugated material contained from one to three molecules of TNF coupled per molecule of antibody and no free TNF.

Non-conjugated antibody was removed from the TNF conjugated antibody by affinity chromatography using CNBr sepharose coupled to a murine anti-TNF antibody. The resin was poured into a small column (1×4 cm) and pre-equilibrated with 10 mM phosphate buffer, pH 7.2 containing 0.1 M NaCl. After loading the S-300 pooled sample, the column was washed with 30 ml of the same buffer to completely elute non-conjugated antibody. TNF-conjugated antibody bound to the column.

Figure 2:
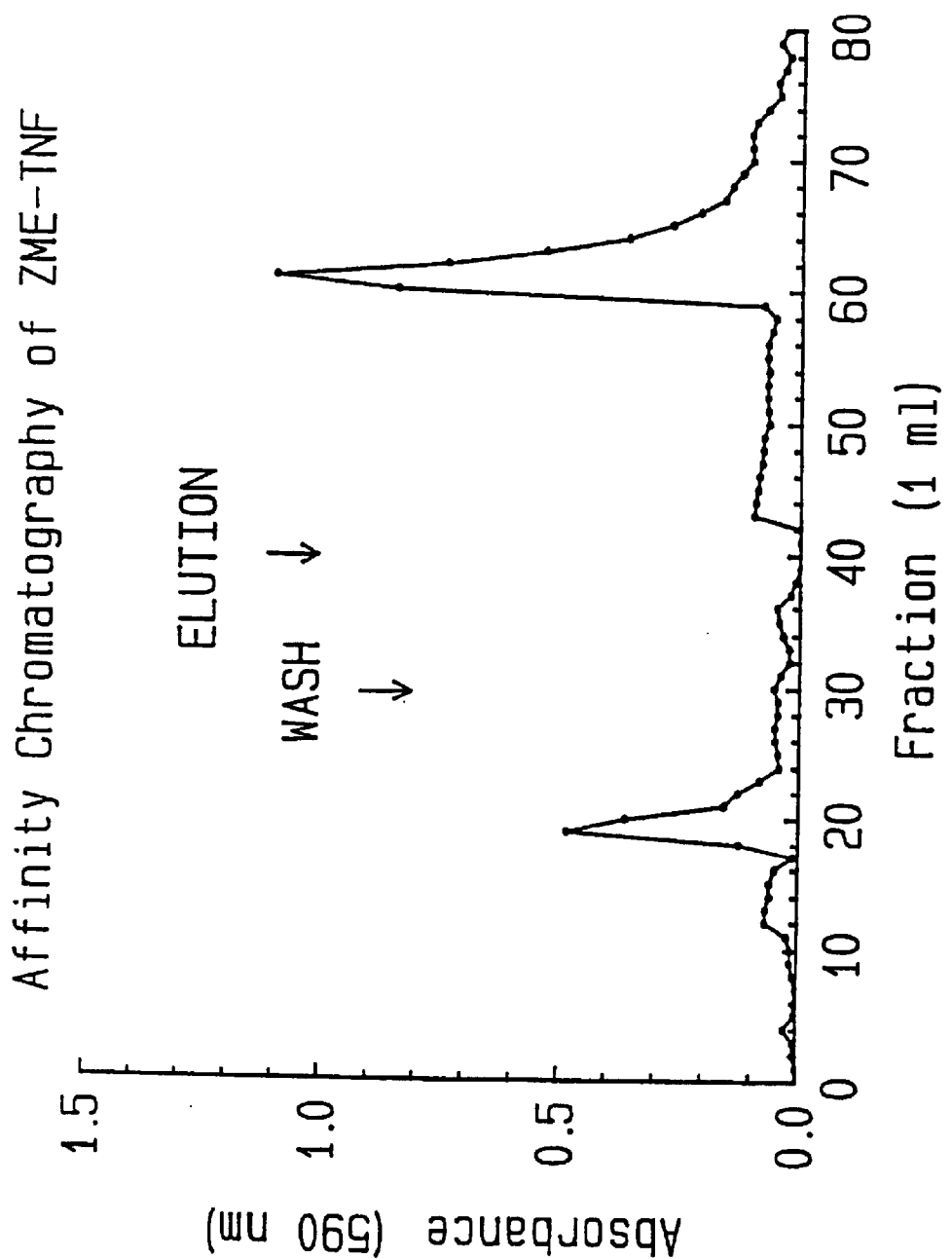
FIG. 2 demonstrates the chromatographic profile of the pooled fractions from the S-300 chromatography after affinity chromatography.

The antibody-TNF complex eluted from the column as shown in FIG. 2 which depicts the elution profile of the TNF affinity column. The flow-through peak contains only free antibody while fractions 58–70, contain antibody-TNF conjugate free of unconjugated TNF or antibody. The pooled fractions from the S-300 chromatography were applied to an affinity chromatography support to which an anti-TNF murine antibody was bound. The column was washed extensively with PBS allowing free ZME antibody (Fraction 20 peak) to elute from the resin. Elution of ZME-TNF conjugate was performed by washing the column with 0.1 M Na acetate buffer (pH 4.5) containing 0.15 M NaCl buffer. As shown in FIG. 2, the purified conjugate was eluted as a single protein peak. PAGE analysis on a 5–20% acrylamide continuous gradient non-reducing gel demonstrated that the conjugate contained ZME bound to 1, 2 and 3 TNF molecules. There was no detectable free TNF or free ZME-018 in the final product. Protein content of the eluted fractions was determined by the Bradford dye binding assay. The protein-containing fractions were pooled and the elution pattern confirmed by electrophoresis on a 5 to 20% gradient non-reducing polyacrylamide gel.

The L-929 assay described in Example 2 was utilized to estimate the TNF activity of the essentially pure TNF-antibody complex. Both the essentially pure 15A8-TNF and the ZMF-TNF antibody conjugates are active in the L-929 assay. A 1:1000 dilution of the original sample caused approximately a 50% inhibition of L-929 cell growth. Thus, the activity of the original preparation was 1000 U/ml.

EXAMPLE 8
Binding of TNF-conjugated and Unconjugated ZME-018 Antibody

In order to determine whether changes in the binding characteristics of ZME to target A-375 (antigen positive) cells or T-24 cells (antigen negative) occurred by modification with TNF, cells were plated at 50,000 cells/well in a 96-well plastic plate and allowed to air-dry at room temperature. Various concentrations of ZME or ZME-TNF were added, allowed to bind for 3 hours at room temperature. A standard ELISA assay was performed for detection of murine antibody.

The ability of the TNF-conjugated and unconjugated ZME-018 antibody to bind to target cells was assessed. Fifty thousand target cells (A-325) or non-target Human bladder carcinoma cells (T-24 cells) were added to each well of microtiter plate. The cells were dried on the plates overnight at 37° C. The cells were then washed with three changes of cold PBS and air dried overnight. The cell surface antigenic determinants remain antigenically active.

After attachment of the cells, the plates were washed with Washing Buffer (9.68 g Tris, 64.8 g sodium chloride, 16 ml Tween 20, 800 mg thimerasol in 8 L of double distilled water). Antibody samples were diluted in Washing Buffer containing 1% Bovine serum albumin (w/v) (Diluting buffer). Fifty microliters of various concentrations ranging from 0.002 to 100 ug/ml of either conjugated or unconjugated ZME-018 antibody were added to the wells. After incubation for 1 hour at 4° C., the supernatants were removed and the wells washed twice with Washing Buffer.

Fifty microliters per well of alkaline phosphatase-conjugated goat anti-mouse IgG diluted 1:1000 (v/v) (APGAM) in Diluting Buffer was added to each well. The plates were incubated for 1 hour at 4° C. and the wells washed twice with Washing Buffer. After incubation of the plates with 50 ul of Substrate Solution (80 mM citrate phosphate (pH 5.0), 1 mM ABTS substitute and 4 ul of 30% hydrogen peroxide) in the dark for 30 minutes at room temperature, 25 ul of 4 N sulfuric acid was added to each well. The absorbance at 492 nm was determined on an Elisa plate reader.

Figure 3:
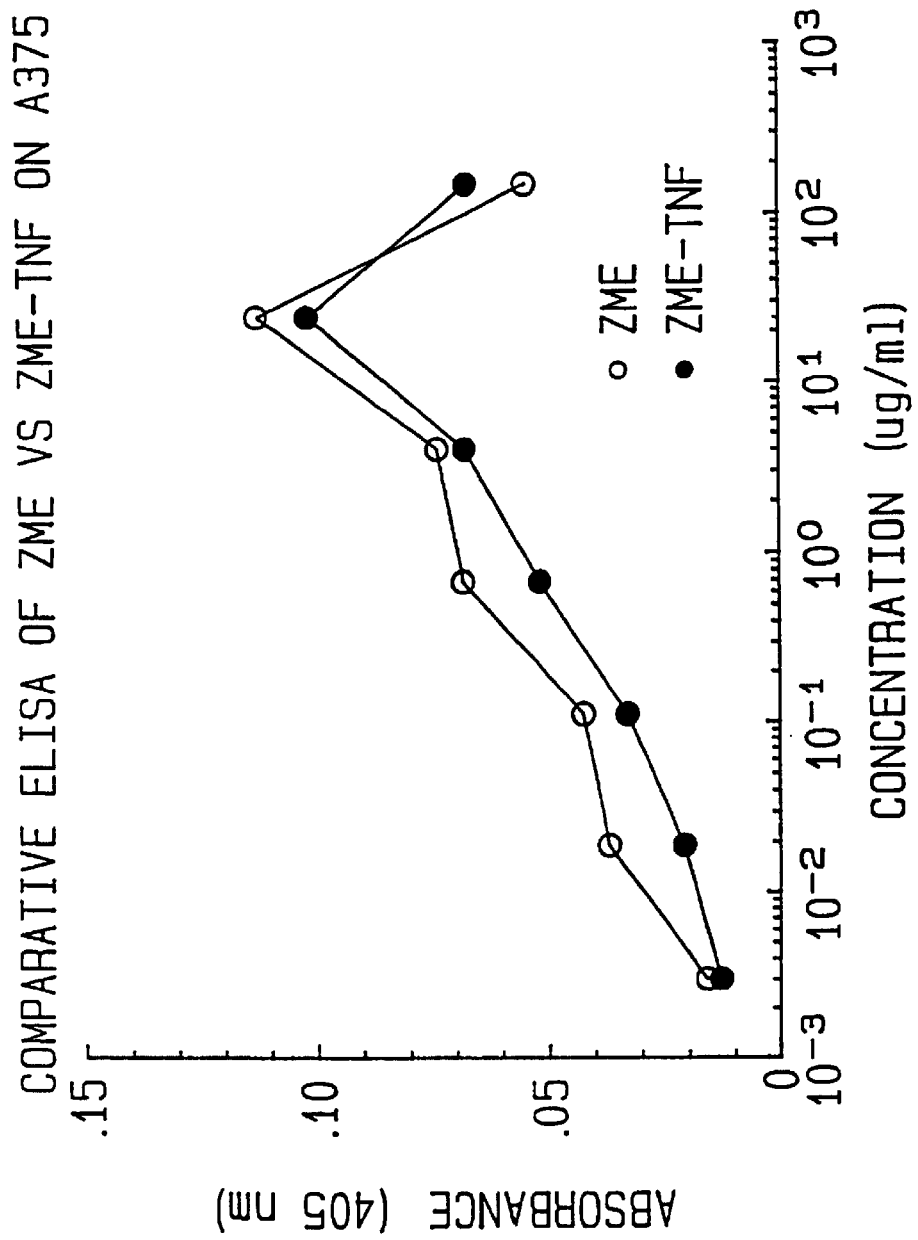
FIG. 3 demonstrates the comparison of the binding of the ZME-018-TNF conjugate and free TNF to target antigen positive A-375 cells and antigen negative T-24 cells.

FIG. 3 shows that the ZME-TNF complex bound to A-375 target cells to the same extent as did native ZME antibody. Since there was no difference in the binding of the ZME-TNF or the unconjugated ZME antibody to the A-135 antigen containing target cells, the chemical conjugation procedure does not alter the affinity of the antibody for its target antigen. There was no detectable binding of either ZME or ZME-TNF complex to non-target T-24 bladder carcinoma cells.

EXAMPLE 9
Effects of TNF and TNF-15A8 or ZME-TNF Antibody Complex

Figure 4:
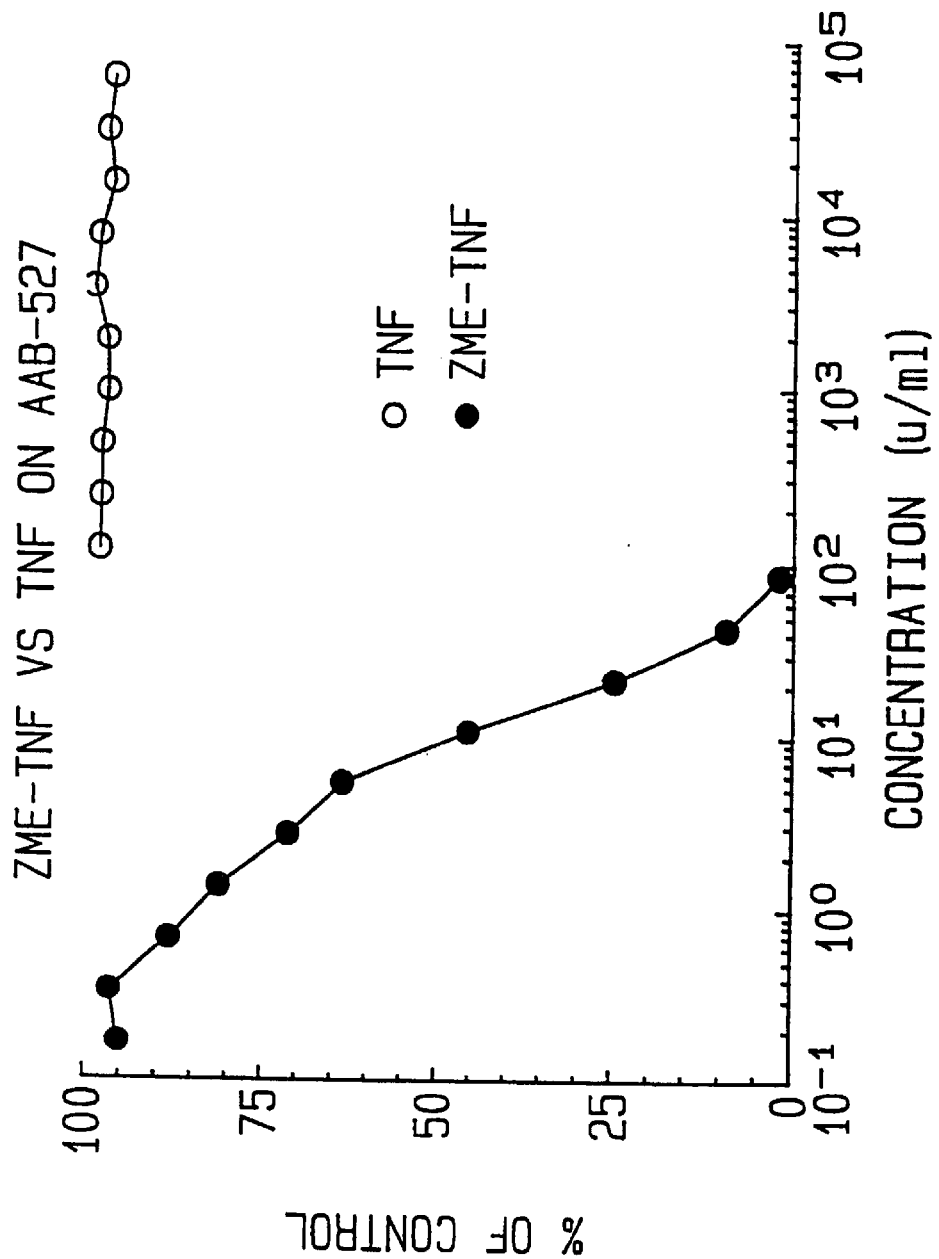
FIG. 4 demonstrates the cytotoxicity of the ZME-TNF immunoconjugate and TNF alone on antigen-positive human melanoma cells (AAB-527).

The antiproliferative effects of TNF and 15A8-TNF or ZME-TNF conjugate were assessed by plating approximately 5,000 log-phase cells/well in 96 well microtiter plate in 200 ml of appropriate tissue culture media. The cells were allowed to adhere for 24 hours at 37° C. in atmosphere of 5% $CO_2$ in air. Non-targeted, antigen negative T-24 human bladder carcinoma cells, Me-180 cells antigen positive for 15A8 and A-375 human melanoma cells antigen positive for ZME-018 in log-phase were treated with various concentrations of either media alone (control), TNF 15A8-TNF conjugate or ZME-TNF conjugate and incubated at 37° C. in an atmosphere of 5% $CO_2$ in air for 72 hours. The plates were washed three times with cold PBS. 50 ml of methanol was added to each well and the cells lysed by repeated cycles of freezing and thawing. Protein concentrations were then determined. Alternatively, cell numbers in each well was assessed using crystal violet stain. The absorbance of each well was determined on an ELISA reader and compared to control wells (no treatment). As shown in FIG. 4, TNF alone had no cytotoxic or cytostatic of TNF used (50,000 units/well). However, with the ZME-TNF conjugate, 50% inhibition was obtained with only 10 units/ml.

Cell growth inhibition was also assessed by reduction in protein concentrations or cell number of treated cells as compared to saline-treated controls. There was no inhibition of cell growth by the 15A8-TNF conjugate or the ZME-TNF T-24 carcinoma on non-targeted T-24 carcinoma cells. There was no effect of 15A8-TNF against the T-24 non-target cell line. Since only cells containing the 15A8 antigen on their surface were killed by the TNF-15A8 immunotoxin, this immunotoxin is an efficient method to target and kill 15A8 tumor associated antigen-containing cells while minimizing or preventing damage or injury to normal non-tumor associated antigen-bearing cells.

Figure 5:
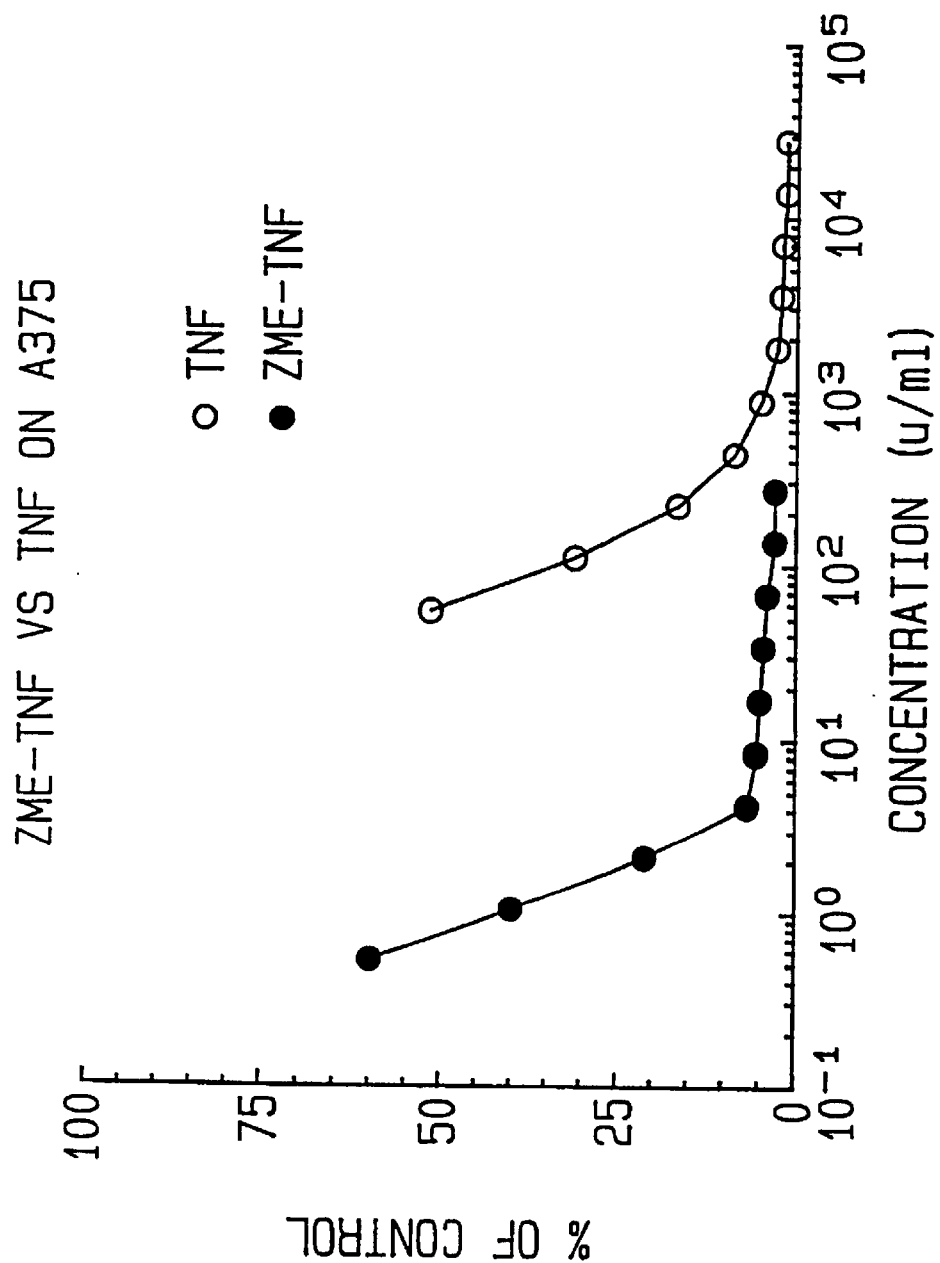
FIG. 5 demonstrates the growth inhibition of the ZME-TNF immunoconjugate on antigen-positive A-375 cells.

The ZME-TNF conjugate was more active than free TNF when tested on antigen-positive human melanoma (either AAB-27 or A-375) cells in culture (FIGS. 4 and 5). As shown in FIG. 4, TNF alone had no effect on the growth of AAB-27 cells at doses up to 50,000 U/ml. However, 50% inhibition was obtained with approximately 6 U/ml of the ZME-TNF conjugates as shown in FIG. 5. A-375 target human melanoma cells were inhibited by TNF alone at doses of approximately 100 U/ml, while the ZME-TNF conjugate inhibited cells at a concentration of approximately 0.8 U/ml. Me-180 target cells were 10 fold more sensitive to the 15A8-TNF immunotoxin than to TNF alone (FIG. 6).

Figure 6:
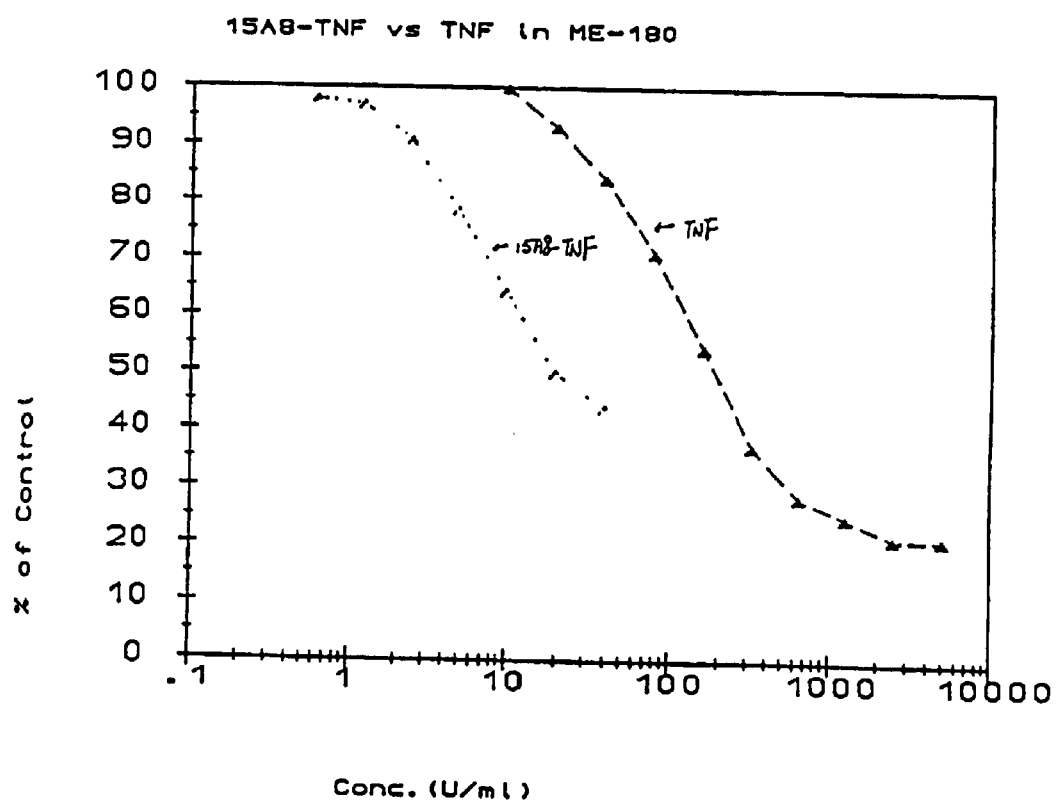
FIG. 6 demonstrates the growth inhibition of the MoAb15A8-TNF immunoconjugate on antigen-positive ME-180 cells.

FIG. 6 demonstrates that at approximately 15 U/ml, TNF conjugated 15A8 antibody inhibited 50% of the Me-180 cells, while a concentration of 200 U/ml of the unconjugated TNF was required to achieve the same effect. There was no effect of either TNF or ZME-TNF conjugate on antigen-negative T-24 cells.

Thus, immunoconjugates of ZME and 15A8 with TNF can dramatically augment the cytotoxicity of TNF on antigen-positive cells while antigen negative cells are unaffected. In addition, in one cell line totally resistant to the growth-inhibiting effects of TNF alone (FIG. 4), cellular resistance can be overcome by antibody targeting.

EXAMPLE 10

The reagents 2-iminothiolane and N-succimindyl 3-(2-pyridyldithio) (proprionate) (SPDP) were obtained from Sigma Chemical Co. Ethylenediamine tetraacetic acid (EDTA), disodium salt was purchased from Boehringer Mannheim. Triethanolamine hydrochloride was obtained from Kodak Chemical Co. and dimethyl formamide (DMF) was purchased from Aldrich Chemical Co. Trizma HCl was obtained from Bio-Rad Laboratories. Recombinant human tumor necrosis factor (0.5 mg/ml, specific activity $3 \times 10^7$ Units/ml) was obtained from Genentech Inc. Antibody ZME-018 was a generous gift of Hybritech Inc. Dulbecco's modified Eagle's medium was obtained from Cellgro (Washington, D.C.). Minimum Essential Medium (MEM) was obtained from Gibco Laboratories (Grand Island, N.Y.). Fetal bovine serum purchased from Hyclone, Inc. Horseradish peroxidase conjugated goat anti-mouse antibody for ELISA was purchased from Bio-Rad Laboratories.

EXAMPLE 11
Cells

Human melanoma (A375-M) cells were obtained from Dr. I. J. Fidler of M. D. Anderson Cancer Center, Houston, Tex. The A375-M cells were routinely grown at a density of $7 \times 10^6$ cells per T-75 flask in Dulbecco's MEM 10% FBS containing gentamicin (0.05 mg/ml), added sodium pyruvate (100 mM), nonessential amino acids (10 mM), glutamine (200 mM) and MEM vitamins. The cells were routinely subcultured twice per week. Murine L-929 cells were purchased from the American Type Culture Collection and were grown in Dulbecco's MEM, 10% FBS containing gentamicin (0.05 mg/ml) and added glutamine (200 mM). All cells were routinely tested and found to be free of mycoplasma contamination using the Gen-Probe assay kit.

EXAMPLE 12
Conjugation of ZME-018 With TNF

Two ml of ZME-018 (4.85 mg/ml) in PBS was added to a 12×75 mM glass tube. A solution of SPDP (6 mg/ml) in dry DMF was added while vortexing at five-fold molar excess. The mixture was incubated for 30 minutes as room temperature and excess unreacted SPDP was removed by gel filtration on a Sephadex G-25 column (2×30 cm) equilibrated with 100 mM sodium phosphate, ph 7, containing 0.5 mM EDTA (Buffer A). The void volume peak containing protein was pooled and held on ice.

Five mg of TNF (0.5 mg/ml) in a 16×100 mM glass test tube was added to stock solutions of TEA/HCl and EDTA to a final concentration of 60 mM TEA/HCl, 1 mM EDTA (ph 8.0) and 2-iminothiolane was added to a final concentration of 5 mM. The sample was incubated for 90 minutes at 4° C. under a stream of N2. Excess iminothiolane was removed by gel filtration on a BioRad P-6 (2×40 cm) column pre-equilibrated with 5 mM bis-Tris acetate buffer (pH 5.8) containing 50 mM NaCl and 1 mM EDTA (Buffer B). The modified TNF eluting in the void volume was pooled and kept at 4° C.

Modified ZME-018 in Buffer A was mixed with modified TNF in Buffer B in a molar ratio of 1:10. The pH of the mixture was adjusted to 7.0 by addition of 0.5 M TEA/HCl (pH 8.0) and the mixture was incubated for 20 hours at 4° C. The reaction mixture was purified by chromatography on Sephacryl S-300HR (Pharmacia). High molecular weight fractions were pooled and further purified by chromatography on an affinity column.

The affinity support for TNF was prepared by first dialyzing 300 μg of anti-TNF murine antibody (TNF-beta, supplied by Genentech Inc.) in 0.1 M $NaHCO_3$ buffer, pH 8.5. One ml of affigel-10 resin (from BioRad) was transferred to a 5 ml centrifuge tube and washed 3× with cold (4° C.) deionized $H_2O$. The antibody and the resin were admixed and gently agitated at 4° C. for 24 hours. The resin was washed and remaining active ester groups were blocked by the addition of 1 ml of 0.1 M NaHCO$_3$ pH 8.0 and 0.1 ml of 1 M ethanolamine. The high molecular weight fractions from S-300 chromatography (Fractions 35–55) were pooled and applied to an anti-TNF affi-gel column (1 cm×5 cm) equilibrated with PBS. The sample was loaded and washed with 50 ml of PBS to elute free antibody. TNF conjugated to ZME was eluted by the addition of 50 mM sodium citrate buffer (pH 3.0) containing 150 mM NaCl. The column effluent was fractionated using a Gilson fraction collector (model FC-80). Protein analysis of the various fractions was performed using a BioRad protein assay. Fractions from the various steps were analyzed by silver-stained SDS-PAGE using a 5–15% acrylamide gradient gel. The biological activity of the ZME-TNF immunoconjugate was determined using the standard bioassay for TNF activity examining cytotoxicity against murine L-929 cells in culture.

EXAMPLE 13
ELISA Assay of ZME and ZME-TNF Conjugate

An ELISA was performed to determine the immunoreactivity of the ZME-TNF conjugate compared to ZME alone. Briefly, 5×10$^4$ melanoma cells (A375-M) per well were added to 96 well polyvinyl microtiter plates (Falcon). The plates were dried for 18 hours at 37° C. and then washed twice with 10 mM PBS ph 7.4 containing 0.1% Tween-20 and 0.02% Thimersol (washing buffer). Antibody ZME-018 or ZME-TNF conjugate were diluted in washing buffer containing 0.1% BSA, added to each well and plates were incubated for one hour at room temperature. After three washes with washing buffer, 50 µl of 1:1000 dilution horseradish peroxidase-conjugated goat anti-mouse IgG (BioRad) was added to each well and incubated for one hour at room temperature. After three washes, 100 µl of substrate (1 mM ABTS containing 1 µl/ml of 3% H$_2$O$_2$) was added to each well. The reaction was stopped after 10–20 minutes by addition of 5% SDS in PBS and absorbance at 405 nm was measured with an ELISA reader.

EXAMPLE 14
In vitro Cytotoxicity of TNF and ZME-TNF

To illustrate the cytotoxicity of ZME-TNF and TNF, antigen-positive human melanoma cells (A375-M) in MEM, 10% fetal bovine serum were plated into 96 well plates at a density of 5×10$^3$ cells well and allowed to adhere for 24 hours at 37° C. in 5% CO$_2$. After 24 hours, the media was replaced with media containing different concentrations of either TNF or ZME-TNF conjugate. The effect of TNF-α and ZME-TNF on the growth of tumor cells in culture was determined by crystal violet staining. After incubating the plates with TNF and ZME-TNF for 72 hours at 37° C., medium was aspirated, and the cell monolayers were rinsed three times with PBS. Following the final rinse, cells were fixed and stained by the addition of 0.5% crystal violet in 20% methanol (0.1 ml/well). The plates were rinsed three times in deionized water and crystal violet was extracted from adherent cells by the addition of 0.2 ml of Sorenson's buffer/well (0.1 M sodium citrate, ph 4.2, in 50% ethanol). Cell plates were vortexed for 30 minutes at room temperature and the absorbance was read at 540 nm (Bio-Tek Instruments, Winooski, Vt.) and compared with control wells (medium alone). Values shown are the mean of duplicate experiments performed in octuplicate.

EXAMPLE 15
Tissue Distribution of Radiolabeled ZME-TNF, TNF and ZME Antibody and Antibody-toxin Labeling Using PIB One drawback in the use of $^{125}$I or $^{131}$I labeled protein in vivo is the potential for rapid and extensive dehalogenation. A procedure for radioiodination utilizing monoclonal antibodies which incorporates iodine into protein via a metabolically stable linkage has been previously described. This method conjugates N-succinimidyl para-iodobenzoate to the protein. Briefly, 37.5 ul of 1% HOAC/MeOH, 10 µl of a 1 mg/ml solution of N-chlorosuccinimide (NCS) in MeOH and 10 µl of PBS were sequentially added to a reaction vial fitted with a rubber septum containing N-succinimidyl 4-tri-n-butylstannylbenzoate (Neorx Corp., Seattle, Wash.) (12.5 mg) in 12.5 µl of HOAC/MeOH. One mCi of $^{125}$I was added to the reaction solution and after 5 minutes, the reaction was quenched by addition of 10 µl of 0.1 M NaHSO$_3$. The MeOH solvent was evaporated under a N$_2$ stream for 10 minutes. Five hundred µg of protein in 100 µl PBS was mixed with 100 µl 0.5 M, of borate buffer (ph 9.3) and then added to the reaction vial. The conjugation was allowed to proceed for 5 minutes at room temperature. Unreacted radioiodine was removed by chromatography on a Sephadex G-25 (PD-10) column (Pharmacia LKB Biotechnology, Piscataway, N.J.). Radiochemical yield was from 40–60%. Incorporation of radiolabel into protein measured by TCA precipitation was greater than 90%. The specific activity of radiolabeled proteins ranged between 0.2–0.4 Ci/µg.

EXAMPLE 16
Immunoreactivity Assay

The immunoreactivity of radiolabeled ZME and ZME-TNF was evaluated using the method of Lindmo et al., *J Immunol Methods* 72:77 (1984). Briefly, melanoma cells (2×10$^6$ A375-M) were incubated with various concentrations of $^{125}$I-labeled antibody or immunoconjugate for 1 hour at 4° C. The cells were washed with PBS containing 1% BSA, lysed with 2% NP-40 (Sigma) and counted in a gamma counter (Packard model 5360). The immunoreactivity values ranged from 40–60% for both ZME-TNF immunoconjugate and ZME-018 monoclonal antibody.

EXAMPLE 17
Tissue Distribution Study

Four to six week old athymic (nu/nu) mice were obtained from Harlan Sprague Dawley, Indianapolis, Ind. The animals were maintained under specific pathogen-free conditions and were used at 6–8 weeks of age. Animals were injected subcutaneously, (right flank) with 2×10$^6$ log phase. A375-M melanoma cells and tumors were allowed to establish for three weeks. Monoclonal antibodies and immunoconjugates were labeled with $^{125}$I 24 hours prior to injection at a specific activity 0.3 ci/µg protein. After examining the immunoreactivity of the antibody and immunoconjugate, mice were injected (i.v. tail vein) with 5 µCi of label and 10 µg of total protein in 200 µl of normal saline. Mice were sacrificed by cervical dislocation 24 and 72 hours following injection. Samples of blood, tumor, heart, lung, liver, spleen, kidney, intestine and muscle were removed, weighed and assayed for radioactivity in a Packard gamma counter (model 5360). The percentage of injected MAb/g tissue (% ID/g) in tumor and normal organs was calculated. Tumor to blood or tumor to organ ratios were also calculated by dividing the % ID/g Mab in tumor by the % ID/g Mab in the respective organ.

EXAMPLE 18
Pharmacokinetics

Four to six week old BALB/C mice were injected with 0.3 µCi (5 µg) of either labeled Mab ZME-018 or ZME-TNF immunoconjugate; at 15, 30, 45, 60, 75, 90, 105, 120, 240 mins and 24 hours after injection, 2 mice at each time-point were sacrificed by cervical dislocation. Blood samples were removed (chest cavity), weighed and counted to determine total radioactivity in a gamma counter (Packard, model 5360). The blood samples were also centrifuged and plasma was decanted and counted to determine radioactivity. Results from plasma determination of radioactivity were analyzed by a least-square nonlinear regression (RSTRIP, from MicroMath, Inc.) program to determine pharmacokinetic parameters.

EXAMPLE 19
In vivo Efficacy 4 to 6 week old BALB/C nude (nu/nu) mice were injected with $2 \times 10^6$ A375-M log-phase melanoma cells subcutaneously in the right flank. The tumors were allowed to establish for 3 weeks prior to starting therapy and the mice were divided into 3 groups. Each treatment group had 5 mice with 100–200 mm$^3$ established tumors. The mice were injected (i.v. tail vein) with either saline, ZME or ZME-TNF immunoconjugate (10,000 units/injection/mouse) daily for 5 days followed by 10 days off therapy and another course of therapy for 5 days. At the end of therapy, the mice were monitored for additional 30 days.

EXAMPLE 20
Cytotoxicity of ZME-TNF in vitro

Figure 7:
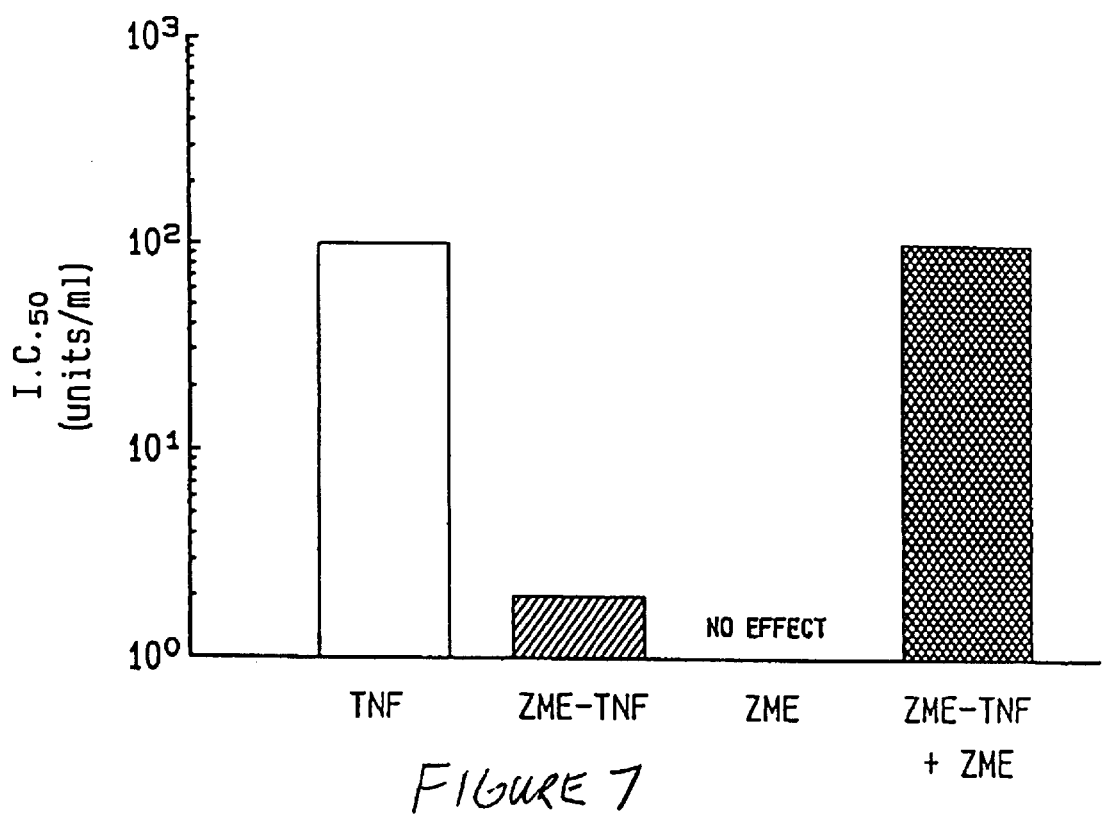
FIG. 7 shows the antiproliferative effect of TNF (O-O) and ZME-TNF (O-O) on A375-M melanoma cells with and without free Mab ZME-018. Various concentrations of TNF & ZME-TNF were added to log-phase cells and incubated for 72 hours at 37° C.

Dose response curves for TNF alone or ZME-TNF against A-375 cells in log phase are shown in FIG. 7. The concentrations required to inhibit cell growth by 50% of control values were 100 U/ml of free TNF but only 2 U/ml of the ZME-TNF conjugate. Co-administration of ZME antibody (50 μg/ml) with ZME-TNF conjugate shifted the IC$_{50}$ values of ZME-TNF conjugate to that of free TNF alone suggesting that the augmented cytotoxicity observed with the antibody conjugate may be due to its interaction with the gp-240 antigen on the cell surface. Since addition of ZME alone to these cells had no appreciable cytotoxic or cytostatic effects, the TNF component of the conjugate appears to be alone responsible for the cytotoxic events observed.

EXAMPLE 21
In vivo Pharmacokinetics of ZME, TNF and ZME-TNF Conjugate

Figure 8:
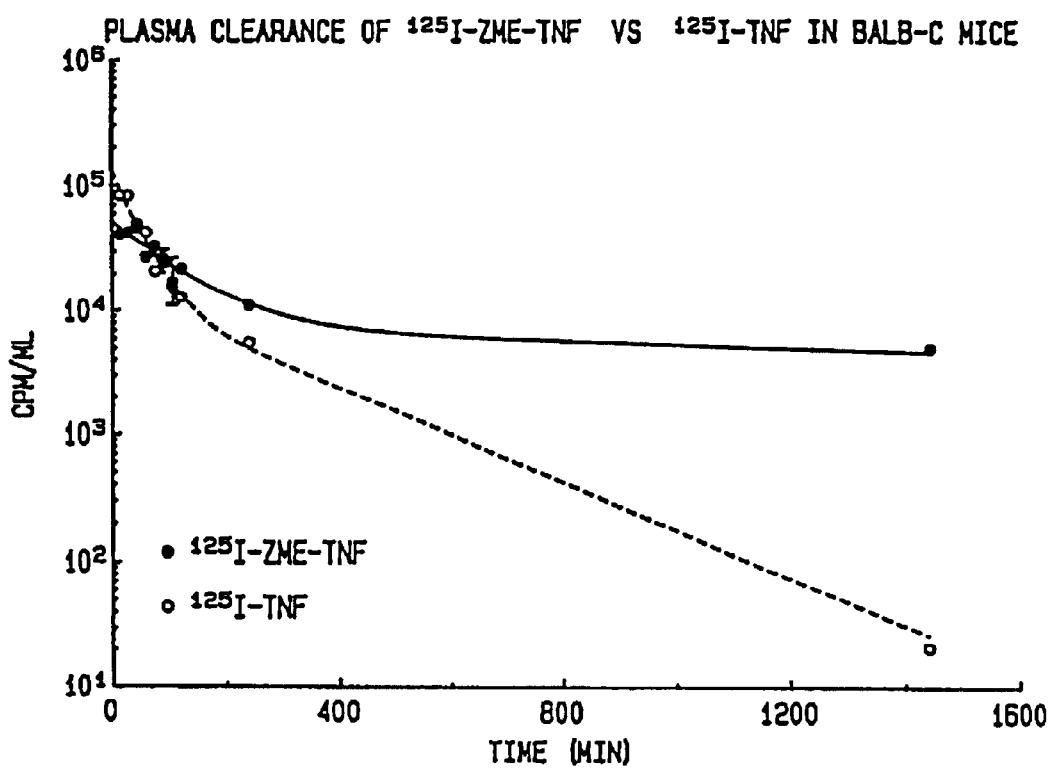
FIG. 8 shows the plasma clearance of radiolabeled-TNF and ZME-TNF conjugate. The Figure shows the data points and best fit least square line through the data points. Both curves are biphasic with TNF clearance significantly faster than ZME-TNF conjugate.

As described above, ZME, TNF, and the ZME-TNF immunoconjugate were radiolabeled using the PIB method described above. FIG. 8 shows the plasma clearance of both radiolabeled TNF and ZME-TNF conjugate. The clearance of both agents as well as that of native ZME was biphasic and closely fit (r2>0.94) an open, two compartment mathematical model. As shown in Table I, the half-lives for ZME and ZME-TNF were similar with alpha phase half lives of 83.5 and 72 minutes respectively. In addition, the beta-phase half lives were also similar at 41.3 and 36.1 hours respectively. In contrast, the clearance of free TNF was relatively rapid with alpha and beta phase half lives of 27.1 minutes and 2.7 hours, respectively. The immediate apparent volume of distribution (Vd) for ZME alone approximated the blood volume (1.9 ml) while TNF alone had a somewhat larger Vd suggesting a greater distribution outside the vasculature. The ZME-TNF conjugate displayed a higher Vd than either ZME or TNF suggesting a more extensive extravascular disposition than either of its component agents. The area under the concentration curve (Cxt) for TNF was substantially lower than that of ZME alone (3.51 vs 139.6 μCi/ml×minute) due to its relatively short plasma half life. The Cxt for ZME-TNF was substantially larger than that of TNF (3 fold) and approximately 10 fold lower than that of ZME because of its relatively greater distribution outside the vasculature.

Figure 9:
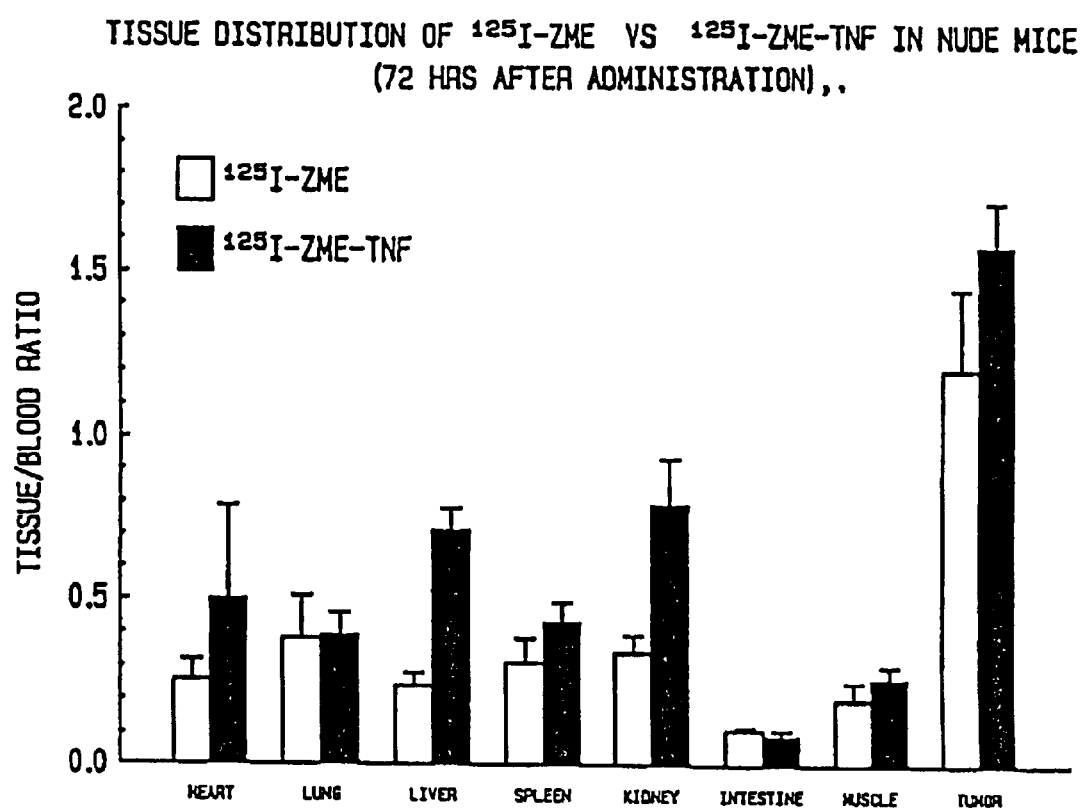
FIG. 9 shows the tissue distribution of radiolabeled antibody as well as conjugate in tumors compared to other organs.

EXAMPLE 22
Tissue Disposition of ZME and ZME-TNF in a Melanoma Xenograft Model Radiolabeled ZME or ZME-TNF were each administered to groups of 5 nude mice bearing subcutaneous, well-developed human melanoma (A375-M) xenografts. Seventy-two hours after administration, the animals were sacrificed and tissue and blood samples were analyzed for radioiodine content as described above. As shown in FIG. 9, uptake of $^{125}$I ZME was highest in tumor tissue with smaller amounts found in lung, spleen, kidney, heart and liver. After administration of $^{125}$I-ZME-TNF, the uptake of radiolabel was highest in tumor tissue followed by kidney, liver heart spleen and lung. Compared to the tissue distribution found for ZME, the conjugate displayed an increased concentration primarily in liver and kidney suggesting that these sites may be primarily responsible for the increased Vd of the conjugate compared to that of native ZME.

EXAMPLE 23

Figure 10:
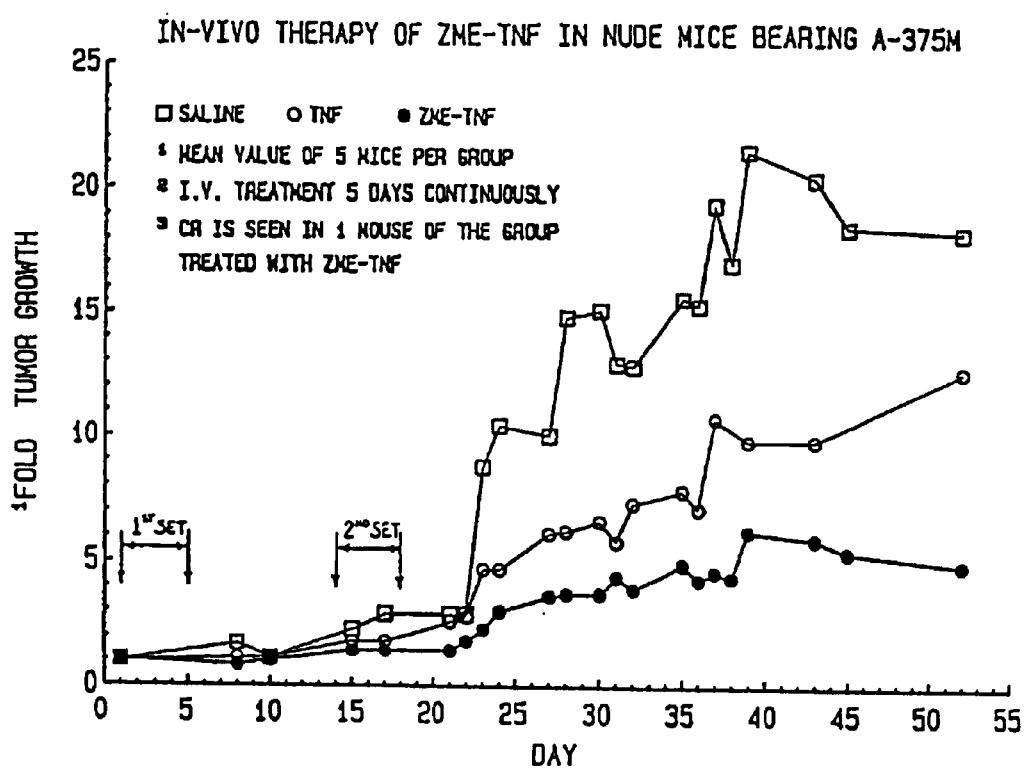
FIG. 10 shows the growth suppression of well established human melanoma (A375-M) tumors in athymic (nu/nu) mice. Tumor cells were innoculated subcutaneously and tumor growth monitored up to day 55. 75% and 50% tumor growth suppression was observed in the group of mice treated with ZME-TNF conjugate compared to saline and Mab ZME-alone respectively.

In vivo Antitumor Effects of TNF and ZME-TNF Groups of mice bearing well-developed (100 mm$^3$) A375-M xenografts were treated (i.v. tail vein) with either saline, TNF (500,000 u/mouse/day) or ZME-TNF (500,000 u/mouse/day) daily for 5 days followed by no treatment for 10 days and then another course of daily injections for 5 days. Mice were observed and their tumors were measured daily. As shown in FIG. 10, tumors in the saline treated mice increased by over 20 fold by day 40 and stabilized in size thereafter. The TNF treated mice showed a delay in growth increasing by 12 fold over the initial tumor volume by day 53. At termination, tumors in all animals in this group were clearly increasing in volume. In contrast, mice treated with the ZME-TNF conjugate showed only a modest 5 fold increase in tumor volume by day 40 and were clearly decreasing in size. One mouse in this group showed a complete disappearance of the tumor nodule.

As shown in the present invention, TNF has a relatively short serum half-life (2 hours) compared to monoclonal antibodies (typically 40 hours). The ZME-TNF immunoconjugate also demonstrates a much longer serum half-life thereby increasing the circulating time of biologically active TNF. In addition to these properties, the incorporation of a tumor cell-binding domain to TNF appears to increase the cytotoxic properties of TNF in culture.

ZME may have a higher affinity for the gp240 surface antigen than TNF has for its receptor. The ZME-TNF conjugate may then provide for a prolonged surface contact thus holding active TNF at the cell surface for protracted interaction with its surface receptor compared to free TNF. Also, there are far more gp240 surface sites per melanoma cell (100,000–1,000,000) compared to TNF receptor sites per cell (1,000–2,000). Therefore, more TNF may be bound per cell after ZME-TNF than after TNF addition. The ZME-TNF conjugate seems to require only a 1–2 hour contact to produce cytotoxicity. Therefore, the improved performance of the conjugate may be due to its increased number of cell binding sites and increased affinity for cells compared to native TNF.

The present invention demonstrates that the conjugates described herein localize within human tumor xenografts and that therapeutic effects can be observed after systemic administration. It should be noted that these antitumor effects were observed in the absence of any apparent toxicity.

All patents and publications mentioned in this specification are indicative of the levels of those skilled in the art to which the invention pertains. Any patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claim is:

1. A conjugate, comprising a ZME-018 antibody targeting a cell surface associated antigen and a biological response modifier moiety selected from the group consisting of TNF-alpha, TNF-beta and interleukin-1.

2. The conjugate of claim 1, wherein said moiety is cytotoxic.

3. The conjugate of claim 1, wherein said moiety is tumor necrosis factor.

4. The conjugate of claim 1, wherein said conjugate is a gene-fusion product recombinantly produced by fusion of a gene coding for the antigen recognition site of a monoclonal antibody with a gene coding for a biological response modifier.

* * * * *